(12) United States Patent
Bolognia

(10) Patent No.: US 10,629,574 B2
(45) Date of Patent: Apr. 21, 2020

(54) COMPACT INTEGRATED DEVICE PACKAGES

(71) Applicant: ANALOG DEVICES, INC., Norwood, MA (US)

(72) Inventor: David Frank Bolognia, North Andover, MA (US)

(73) Assignee: Analog Devices, Inc., Norwood, MA (US)

( * ) Notice: Subject to any disclaimer, the term of this patent is extended or adjusted under 35 U.S.C. 154(b) by 0 days.

(21) Appl. No.: 15/638,083

(22) Filed: Jun. 29, 2017

(65) Prior Publication Data

US 2018/0122784 A1  May 3, 2018

Related U.S. Application Data

(60) Provisional application No. 62/413,867, filed on Oct. 27, 2016.

(51) Int. Cl.
| | |
|---|---|
| *H01L 25/16* | (2006.01) |
| *A61B 5/00* | (2006.01) |
| *H01L 25/18* | (2006.01) |
| *H01L 25/10* | (2006.01) |
| *H01L 23/13* | (2006.01) |
| *H01L 23/498* | (2006.01) |

(52) U.S. Cl.
CPC ............ *H01L 25/16* (2013.01); *A61B 5/6852* (2013.01); *H01L 25/10* (2013.01); *H01L 25/18* (2013.01); *A61B 2562/242* (2013.01); *H01L 23/13* (2013.01); *H01L 23/4985* (2013.01)

(58) Field of Classification Search
CPC . H01L 25/16; H01L 23/5387; H01L 23/5389; A61B 5/6852–6856
See application file for complete search history.

(56) References Cited

U.S. PATENT DOCUMENTS

| | | |
|---|---|---|
| 3,724,274 A | 4/1973 | Millar |
| 3,949,274 A | 4/1976 | Anacker |
| 4,742,183 A | 5/1988 | Soloway et al. |

(Continued)

FOREIGN PATENT DOCUMENTS

| | | |
|---|---|---|
| DE | 10 2011 001 422 A1 | 9/2012 |
| GB | 2528251 A | 1/2016 |

(Continued)

OTHER PUBLICATIONS

Images obtained on Jun. 13, 2011 from a web search related to three-dimensional packaging.

(Continued)

*Primary Examiner* — Tuan A Hoang
(74) *Attorney, Agent, or Firm* — Knobbe, Martens, Olson & Bear, LLP

(57) ABSTRACT

Compact integrated device packages are disclosed. The package comprises a package substrate, a first integrated device die, and a second integrated device die. The first die and the second die are mounted and electrically connected to a first segment and a second segment of the package substrate respectively. The substrate comprises a bendable segment disposed between the first and second segment and can bend so as to angle the first die relative to the second die.

23 Claims, 8 Drawing Sheets

(56) References Cited

U.S. PATENT DOCUMENTS

| | | | |
|---|---|---|---|
| 4,928,206 A * | 5/1990 | Porter | H05K 1/189 165/104.33 |
| 5,126,286 A | 6/1992 | Chance | |
| 5,405,337 A | 4/1995 | Maynard | |
| 5,452,182 A * | 9/1995 | Eichelberger | H01L 21/67144 174/254 |
| 5,554,806 A | 9/1996 | Mizuno et al. | |
| 5,555,159 A | 9/1996 | Dore | |
| 5,616,863 A | 4/1997 | Koen | |
| 5,644,230 A | 7/1997 | Pant et al. | |
| 5,731,222 A | 3/1998 | Malloy et al. | |
| 5,833,608 A | 11/1998 | Acker | |
| 5,903,440 A | 5/1999 | Blazier et al. | |
| 6,040,624 A | 3/2000 | Chambers et al. | |
| 6,075,708 A | 6/2000 | Nakamura | |
| 6,078,102 A | 6/2000 | Crane, Jr. et al. | |
| 6,169,254 B1 | 1/2001 | Pant et al. | |
| 6,184,680 B1 | 2/2001 | Shinoura et al. | |
| 6,225,688 B1 * | 5/2001 | Kim | H01L 23/5387 257/686 |
| 6,291,894 B1 | 9/2001 | Farnworth et al. | |
| 6,304,082 B1 | 10/2001 | Gualtieri et al. | |
| 6,339,191 B1 | 1/2002 | Crane, Jr. et al. | |
| 6,348,427 B1 | 2/2002 | Hamada et al. | |
| 6,511,863 B2 | 1/2003 | Farnworth et al. | |
| 6,536,123 B2 | 3/2003 | Tamura | |
| 6,570,246 B1 | 5/2003 | Lee et al. | |
| 6,591,492 B2 | 7/2003 | Farrar | |
| 6,705,005 B1 | 3/2004 | Blazier et al. | |
| 6,721,189 B1 | 4/2004 | Haba | |
| 6,777,261 B2 | 8/2004 | Farnworth et al. | |
| 6,852,607 B2 | 2/2005 | Song et al. | |
| 6,903,465 B2 | 6/2005 | Farnworth et al. | |
| 7,012,812 B2 | 3/2006 | Haba | |
| 7,115,984 B2 | 10/2006 | Poo et al. | |
| 7,202,552 B2 | 4/2007 | Zhe et al. | |
| 7,211,886 B2 | 5/2007 | Hsu et al. | |
| 7,265,719 B1 | 9/2007 | Moosbrugger et al. | |
| 7,301,332 B2 | 11/2007 | Govari et al. | |
| 7,375,009 B2 | 5/2008 | Chua et al. | |
| 7,420,262 B2 | 9/2008 | Bauer et al. | |
| 7,429,788 B2 | 9/2008 | Clayton et al. | |
| 7,467,552 B2 | 12/2008 | MacGugan | |
| 7,839,657 B2 | 11/2010 | Nodine | |
| 8,692,366 B2 | 4/2014 | Xue et al. | |
| 8,836,132 B2 | 9/2014 | Xue | |
| 9,093,360 B2 | 7/2015 | Bolognia | |
| 9,116,022 B2 | 8/2015 | Bolognia | |
| 9,234,736 B2 | 1/2016 | Engel et al. | |
| 9,278,851 B2 | 3/2016 | Xue | |
| 9,332,940 B1 | 5/2016 | Bolognia | |
| 9,475,694 B2 | 10/2016 | Martizon, Jr. et al. | |
| 2003/0120150 A1 * | 6/2003 | Govari | A61B 5/0031 600/424 |
| 2003/0209789 A1 | 11/2003 | Hanson et al. | |
| 2004/0157410 A1 | 8/2004 | Yamaguchi | |
| 2004/0169244 A1 | 9/2004 | MacGugan | |
| 2005/0230795 A1 | 10/2005 | Furuyama et al. | |
| 2006/0151864 A1 | 7/2006 | Anderson et al. | |
| 2006/0261453 A1 | 11/2006 | Lee et al. | |
| 2007/0053504 A1 | 3/2007 | Sato et al. | |
| 2008/0175425 A1 | 7/2008 | Roberts et al. | |
| 2008/0285111 A1 | 11/2008 | Ishii et al. | |
| 2009/0121342 A1 | 5/2009 | Minakawa et al. | |
| 2009/0268019 A1 * | 10/2009 | Ishii | A61B 1/00124 348/65 |
| 2010/0078739 A1 | 4/2010 | Xue et al. | |
| 2010/0090295 A1 | 4/2010 | Zhe et al. | |
| 2010/0155863 A1 | 6/2010 | Weekamp | |
| 2010/0197148 A1 | 8/2010 | Rudisill et al. | |
| 2011/0018143 A1 | 1/2011 | Chua et al. | |
| 2011/0149522 A1 | 6/2011 | Johann et al. | |
| 2013/0023769 A1 | 1/2013 | Tsai et al. | |
| 2013/0313130 A1 | 11/2013 | Little et al. | |
| 2014/0005521 A1 * | 1/2014 | Kohler | A61B 5/064 600/411 |
| 2014/0197531 A1 * | 7/2014 | Bolognia | G06K 9/0002 257/693 |
| 2015/0066007 A1 * | 3/2015 | Srivastava | A61B 17/320068 606/21 |
| 2017/0014198 A1 * | 1/2017 | Gravlee | A61B 42/50 |
| 2017/0164867 A1 * | 6/2017 | Kassab | A61B 5/6851 |

FOREIGN PATENT DOCUMENTS

| | | | |
|---|---|---|---|
| JP | 09121015 A | 5/1997 | |
| JP | 2009-289724 A | 12/2009 | |
| WO | WO 2016/127130 A1 | 8/2016 | |
| WO | WO-2016127130 A1 * | 8/2016 | A61N 1/37288 |
| WO | WO 2016/171597 A1 | 10/2016 | |
| WO | WO 2016171597 A1 * | 10/2016 | H05K 1/028 |
| WO | WO-2016171597 A1 * | 10/2016 | H05K 1/028 |

OTHER PUBLICATIONS

Sensors—HARTING Mitronics, HARTING Pushing Performance, in 2 pages (downloaded from World Wide Web page: harting-mitronics.ch/en/produkte/anwendungen/sensorik/index.php on Jul. 11, 2011).

Office Action issued in Chinese application No. 201710726748.3 dated Sep. 24, 2019.

* cited by examiner

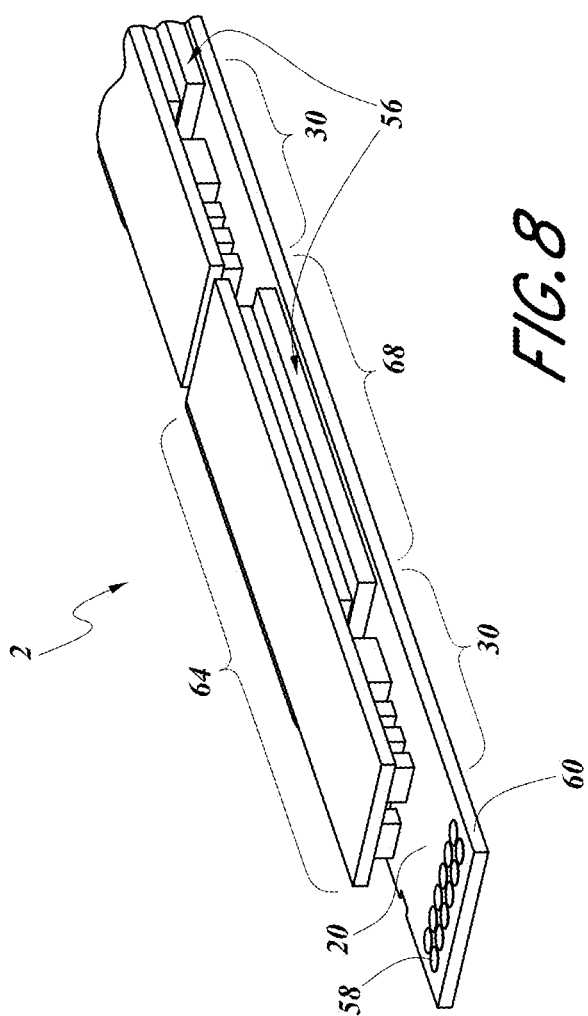

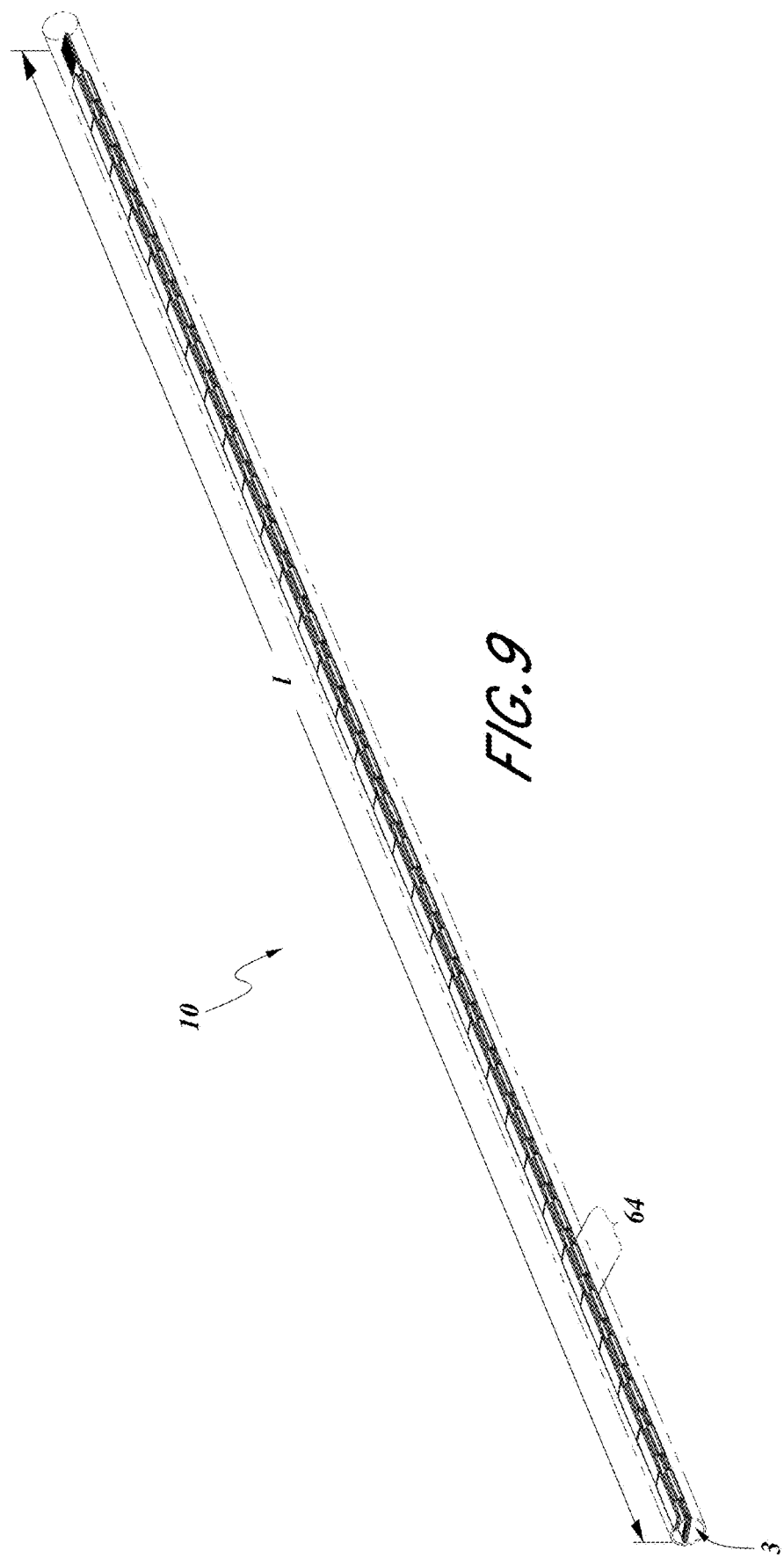

COMPACT INTEGRATED DEVICE PACKAGES

CROSS-REFERENCE TO RELATED APPLICATIONS

This application claims the benefit of U.S. Provisional Application No. 62/413,867, entitled "COMPACT INTEGRATED DEVICE PACKAGES," filed Oct. 27, 2016, the entire disclosure of which is incorporated herein by reference for all purposes.

BACKGROUND

Field of the Invention

The field relates to compact integrated device packages, and, in particular, to compact integrated device packages sized and shaped to be disposed in small form factor systems, such as a catheter assembly.

Description of the Related Art

Many systems utilize elongate structures with small diameter to access various target locations. For example, medical devices may utilize a catheter or other elongate structure to access internal organs of a human patient. In various treatment procedures, a clinician can insert a guidewire through a body lumen of the patient and can deliver a distal end of the guidewire to a treatment location within the patient. In cardiac treatment procedures, such as stent delivery, percutaneous transluminal angioplasty, cardiac ablation, cardiac pumping, or other percutaneous procedures, the clinician can use the Seldinger technique to access the patient's vascular system (e.g., the femoral artery) for insertion of the guidewire. Once the guidewire is placed at the target location, the clinician can insert a catheter system or other elongate structure over the guidewire to guide the catheter system to the treatment site.

For many types of systems, it can be important to provide electrical sensing and/or actuation (e.g., electrical and/or mechanical actuation) in small form factors or small diameter spaces, such as catheter assemblies. However, it can be challenging to incorporate integrated devices in such small spaces. Accordingly, there remains a continuing need for improved compact integrated device packages for various systems, including medical devices.

SUMMARY OF THE INVENTION

In one aspect, an integrated device package sized and shaped to be disposed in a catheter assembly is disclosed. The package can include a package substrate, a first integrated device die mounted and electrically connected to a first segment of the package substrate, and a second integrated device die mounted and electrically connected to a second segment of the package substrate. The first and second device dies are spaced from each other along a longitudinal axis of the package substrate. The package substrate has a bendable segment positioned between the first and second segment. The device package is configured such that, during use of the device package, the bendable segment can bend so as to angle the first device die relative to the second device die at a plurality of orientations.

In some embodiments, the integrated device package can further include a third segment of the package substrate and a third integrated device die is mounted on the third segment. The third segment can bent relative to the first segment along an axis parallel to the longitudinal axis so as to position the third integrated device die at an angle relative to the first integrated device die. In some embodiments, the integrated device package can further include a molding compound between portions of the first and third integrated device dies to mechanically couple the first and third integrated device dies. In some embodiments, the first integrated device die and the third integrated device die define a first device unit. In some embodiments, the package substrate, the first device unit and a second device unit comprises the second integrated device die define a first package module. The integrated device package can further include a second package module including a third device unit comprising fourth and fifth integrated device dies mounted on respective fourth and fifth segments of a second package substrate. The integrated device package can further include a plurality of package modules. In some embodiments, the first package module and the second package module are disposed adjacent one another along an axis transverse to the longitudinal axis.

In another aspect, an integrated device package sized and shaped to be disposed in a small form factor system having a longitudinal axis is disclosed. The device package can include a package substrate, a first integrated device die mounted and electrically connected to a first segment of the package substrate, and a second integrated device die mounted and electrically connected to a second segment of the package substrate. The package substrate is bent such that the first and second dies are disposed between the first and second segments. A lateral dimension of the integrated device package can be less than 6 mm, where the lateral dimension being a dimension transverse to the longitudinal axis.

In some embodiments, the integrated device package can further include a molding compound between at least portions of the first and second integrated device dies to mechanically couple the first and second integrated device dies.

In some embodiments, the package substrate comprises a flexible insulating sheet with embedded conductors.

In another aspect, a package for a catheter assembly is disclosed. The package can include an elongate package substrate having a major longitudinal dimension, a first plurality of electrodes at a distal portion of the elongate package substrate, a second plurality of contact pads at a proximal portion of the elongate package substrate, and a plurality of integrated device dies mounted to the package substrate between the distal and proximate portions of the elongate package substrate. The second plurality is fewer than the first plurality. The plurality of integrated device dies is configured to process signals transduced by the first plurality of electrodes and to transmit the processed signals to the second plurality of contact pads.

In some embodiments, the elongate package substrate comprises a flexible insulating sheet with embedded conductors. In some embodiments, the package substrate is bent at an angle of 170° to 190°.

In another aspect, a method of operating a device comprising an elongate body comprising an integrated device package disposed in a lumen of the elongate body is disclosed. The integrated device package having a first integrated device die mounted to a first segment of a substrate and a second integrated die mounted to a second segment of the substrate. The second segment spaced from the first segment along a longitudinal axis of the elongate body. The method comprising inserting the elongate body into an object, and advancing the elongate body along a non-linear pathway in the object such that, during the advancing, the substrate bends at a bendable segment between the first and second segments so as to angle the first integrated device die relative to the second integrated device die at a plurality of orientations.

In some methods, the elongate body comprises an elongate catheter assembly. In some methods, the inserting comprises inserting the catheter assembly into a patient. In some methods, the advancing comprises advancing the catheter assembly through the vasculature of the patient

BRIEF DESCRIPTION OF THE DRAWINGS

Specific implementations will now be described with reference to the following drawings, which are provided by way of example, and not limitation.

FIG. 8 is a top perspective view of a proximal portion of the package module of FIG. 7.

FIG. 9 is a top perspective view of an integrated device package with two package modules having multiple device units spaced along the longitudinal axis within a catheter assembly.

DETAILED DESCRIPTION OF THE PREFERRED EMBODIMENT

Figure 1:
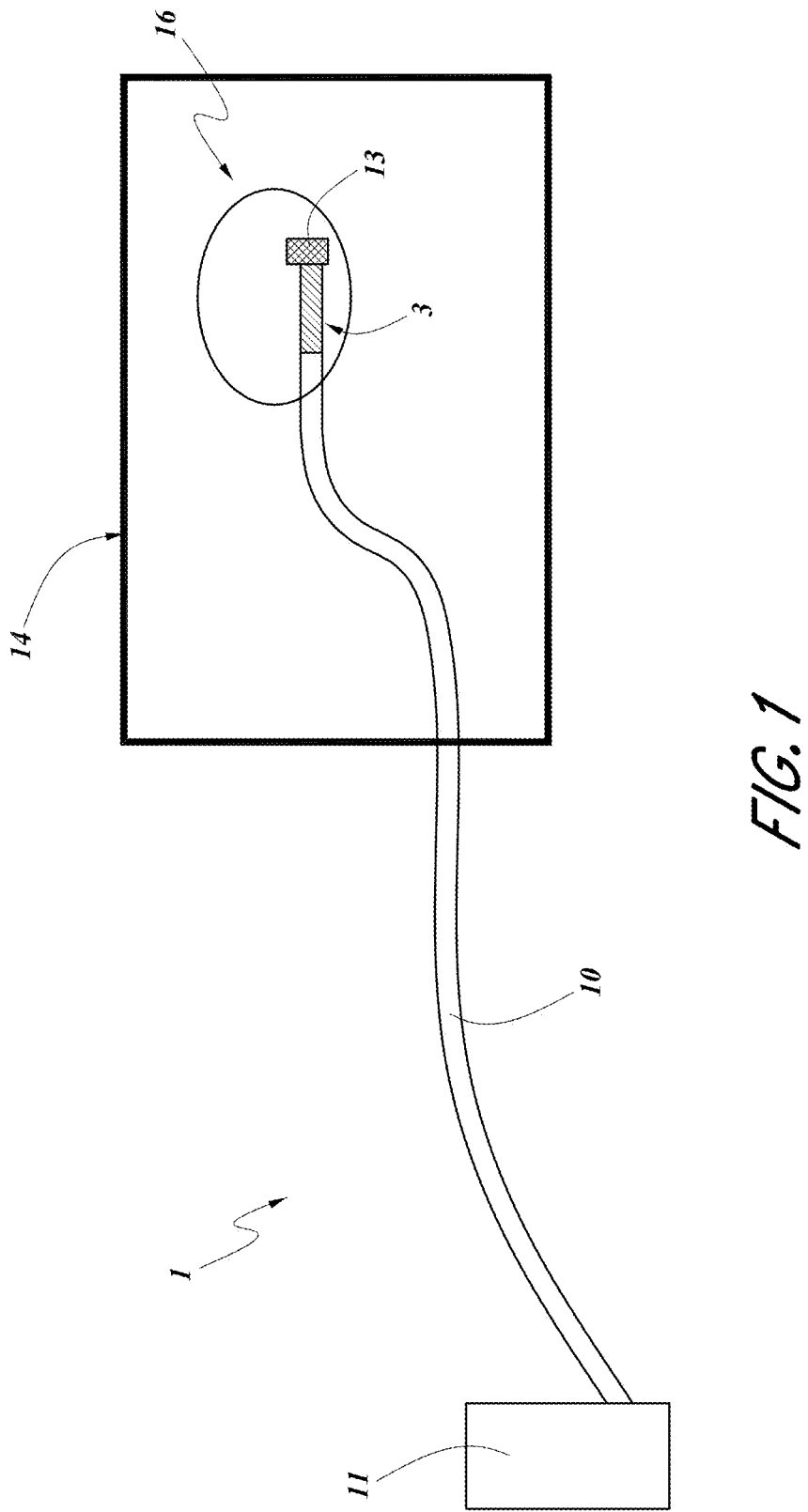
FIG. 1 is a schematic system diagram of a device (such as a medical device) during use in a treatment procedure, according to various embodiments.

Various embodiments disclosed herein relate to integrated device packages sized and shaped to be used in systems that have relatively small diameters or lateral spaces, for example, systems that are configured for insertion into a body lumen or body cavity of a human patient, such as the heart. The embodiments disclosed herein may be particularly beneficial for use with systems that transmit and/or receive signals at a target location (e.g., within the patient), and convey the signals to and/or from processing electronics outside the patient (e.g., a controller of a console). For example, the packages disclosed herein can be used in any suitable type of medical treatment procedure, including, for example, ECG and ablation procedures. It should be appreciated, however, that the packages disclosed herein can be used for any suitable medical treatment procedure, or for non-medical device applications.

In some procedures, a catheter assembly may include sensors, actuators, or other types of devices at a distal portion of the catheter assembly that can interact with a treatment region of the patient. For example, in some embodiments, the distal portion of the catheter assembly can comprise electrical and/or mechanical components (e.g., actuators) that can impart energy to or otherwise act on the treatment region to treat the patient (e.g., a cardiac ablation procedure). In some embodiments, the distal portion can comprise electrical and/or mechanical components that can sense various properties of the patient's anatomy and/or of a treatment procedure. For example, the distal portion can comprise sensors or other components that can transduce physical properties of the patient's anatomy to electrical signals (e.g., electrodes of an ECG device). For example, the distal portion can comprise stents or other components that can physically hold at least a part of the patient's lumen to create an accessible passageway for an operation (e.g., a heart stent procedure).

In some systems, the components of the catheter assembly may communicate with the console outside the body by way of numerous wires that transfer signals to and/or from the components in the catheter assembly (e.g., at the distal portion). The long wires can be stiff and/or can have a large diameter, when bundled together within the catheter assembly. Stiff wires may be undesirable in such systems because, for example, the stiffness can reduce the maneuverability of the device within the anatomy and/or may cause stress to the patient's body.

In some embodiments, the packages disclosed herein can be used in a catheter assembly to transmit and/or receive signals to and/or from components (e.g., a plurality of electrodes) within the catheter assembly (e.g., within the distal portion). A plurality of integrated device dies can process the signals, and can transmit the signals to and/or receive the signals from a plurality of contact pads disposed proximal the integrated device dies. The integrated device dies may perform processes such as amplification, analog-to-digital conversion (ADC), digital-to-analog conversion (DAC), and/or multiplexing. By processing the signals within the catheter assembly, fewer wires may be used to transfer the processed signals to and/or from the console outside the patient's body. Moreover, processing the signals within the catheter assembly can improve signal integrity by reducing the distance over which the analog signals are transferred by wire. The disclosed embodiments can beneficially enable packages that are flexible and small enough to fit within the catheter assembly.

FIG. 1 is a schematic system diagram of a device 1 (such as a medical device) during use in a treatment procedure, according to various embodiments. In this system, the device 1 is inserted into a patient 14. The device 1 can include a catheter assembly 10 that has an integrated device package 3 at a distal portion of the catheter assembly 10, a console 11 outside the patient 14 and in electrical and/or fluidic communication with the catheter assembly 10, and an interactive device 13 mounted to or otherwise electrically communicating with the integrated device package 3. In some embodiments, the interactive device 13 can be part of the integrated device package 3, while in other embodiments, the interactive device 13 may be separate from the integrated device package 3. The interactive device 13 can interact at a target location 16 within the patient 14. The interactive device 13 may include sensors, actuators, or other types of devices that act on and/or transduce information about the target location 16. The interactive device 13 may communicate with the console 11 by transferring signals to and/or from the integrated device package 3. In turn, the package 3 can process the signals and transmit the processed signals to and/or from the console via electrical connectors in the catheter assembly 10. In some embodiments, for example, wires can electrically connect the console 11 to contact pads at a proximal portion of the package 3 within the patient. In other embodiments, the package 3 can comprise an elongate package substrate that extends along the length of the catheter assembly 10 to communicate with connectors outside the patient. In some embodiments, the device 1 can include a wireless communication module that allows the console 11 to wirelessly communicate with the interactive device 13.

For example, the console 11 can comprise a controller that can provide power and/or ground to the device package 3. The controller can comprise processing electronics configured to control the operation of the device 1. For example, the processing electronics can be programmed by way of software to implement instructions that operate the device 1. The console 11 may also include various fluid reservoirs, pumps, sensors, and other devices used in connection with the operation of the device 1. The console 11 can transmit signals to and/or receive signals from the package 3. In various embodiments, the console 11 can comprise a user interface (such as a display or touch-screen display, a keypad, etc.) that informs the clinician about the status of the procedure. The clinician can input instructions to the console 11 by way of the user interface to select various settings and/or operational modes of the device 1 during and/or before use. In some embodiments, the console 11 can be connected to an external processing device (e.g., a computer) that can, for example, act as the user interface and/or analyze operation data. In some embodiments, the console 11 can receive the signals from the package 3, and can provide feedback to the package 3 with further instructions based on the received signals.

Figure 2:
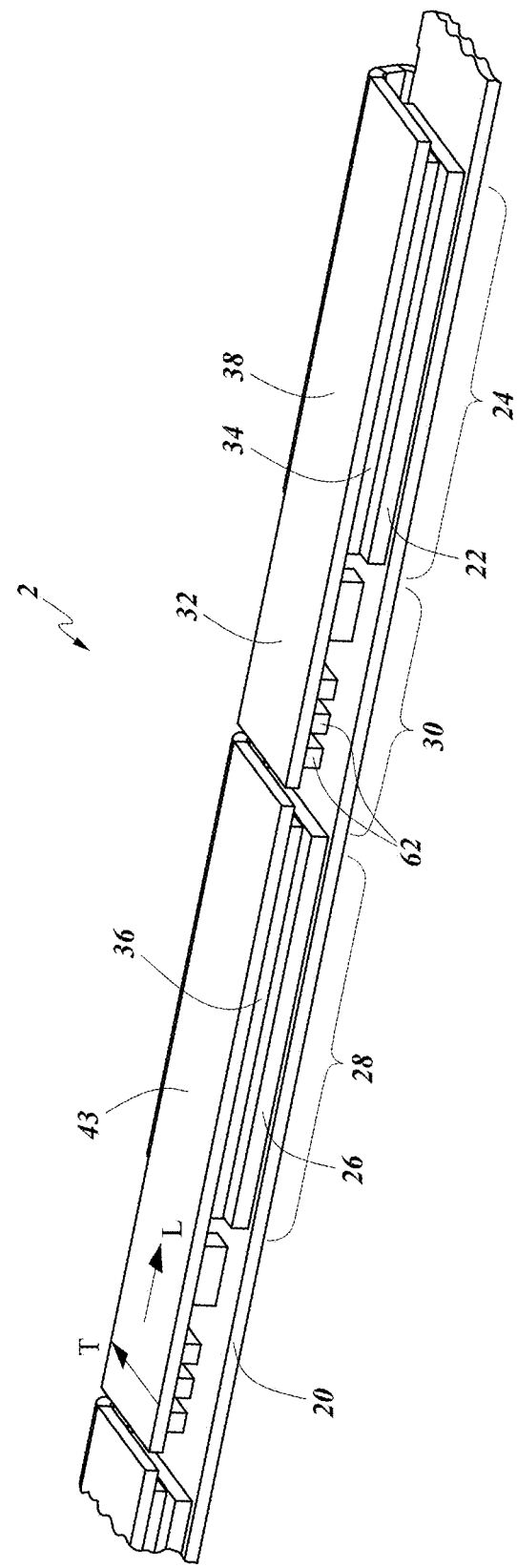
FIG. 2 is a schematic top perspective view of a package module that is sized and shaped to be disposed in a catheter assembly such as that shown in FIG. 1.
Figure 3:
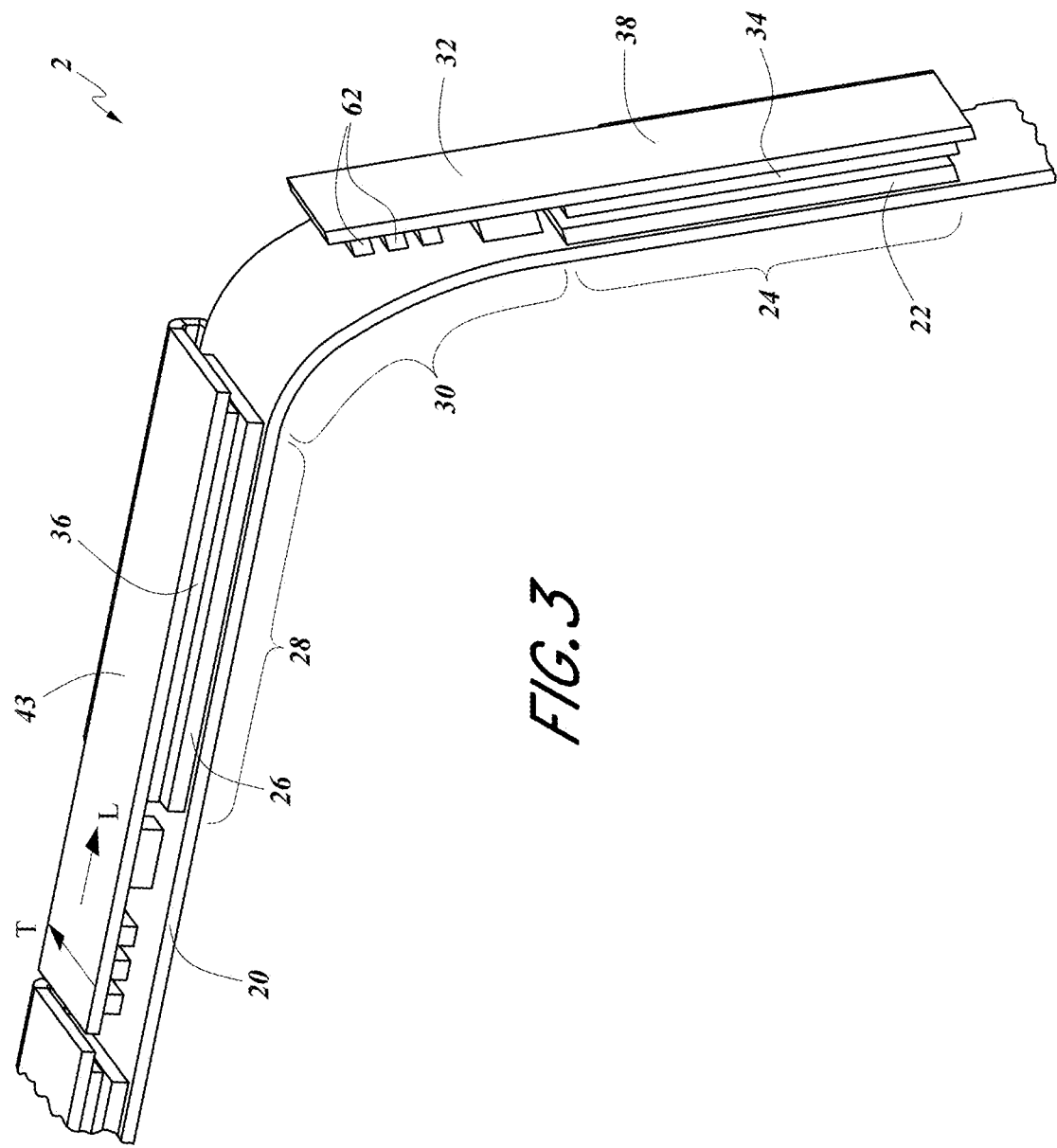
FIG. 3 is a schematic view of the package module of FIG. 2 bent at a bendable segment, such as during use of the catheter assembly.

The package 3 shown in FIG. 1 may comprise one or a plurality of package modules. FIG. 2 is a schematic top perspective view of a package module 2 that is sized and shaped to be disposed in a catheter assembly 10 (FIG. 1) having a longitudinal axis L designed to extend along the length of the catheter assembly 10, and a transverse axis T that is perpendicular to the longitudinal axis L. The longitudinal axis L and the transverse axis T may be defined in local coordinates of the package 3, and may not necessarily correspond to fixed Cartesian coordinates. In FIG. 2, the package module 2 is illustrated in an unbent (or straight) configuration, such as before inserting or maneuvering the catheter assembly 10 through the patient. FIG. 3 is a schematic view of the package module 2 of FIG. 2 bent at a bendable segment 30, such as during use of the catheter assembly 10. The package module 2 may form part or all of the package 3. The package module 2 can include a package substrate 20, a first integrated device die 22 that is mounted and electrically connected to a first segment 24 of the package substrate 20, a second integrated device die 26 that is mounted and electrically connected to a second segment 28 of the package substrate 20, and a bendable segment 30 that separates the first segment 24 and the second segment 28. The package module 2 may also include a third die 34 mounted to a third segment 38, and a fourth die 36 mounted to a fourth segment 43. As shown in FIG. 2, the dies 22, 34 may be disposed between the segments 24, 38, and the dies 26, 36 may be disposed between the segments 28, 43.

The package substrate 20 can comprise a flexible substrate that is configured to be bent at one or a plurality of bendable segments 30 during operation of the device 1. For example, as shown in FIG. 3, during use of the catheter assembly 10, the catheter assembly 10 may be inserted and advanced through the patient's anatomy, which may include a non-linear or curved pathway. As the catheter assembly 10 traverses the non-linear pathway, the catheter assembly 10 and the package 3 can accordingly bend to pass through the anatomy. In various embodiments, the package substrate 20 can comprise a flexible insulator (e.g., polyimide) with embedded metal traces that provide electrical connectivity through the substrate 20. The flexible package substrate can comprise a flexible insulative sheet with multiple conductors embedded therein, separated along the transverse axis T and extending along the longitudinal axis L, and multiple contact pads and/or electrodes exposed at surfaces of the insulative sheet. The package module 2 can be configured such that, during use of the integrated device package 3 in the catheter assembly 10 (see FIG. 3), the bendable segment 30 can bend so as to angle the first integrated device die 22 relative to the second integrated device die 26 at a plurality of orientations. For example, during operation and/or use of the catheter assembly 10, the bendable segment 30 can bend about the transverse axis T at a plurality of angles less than or equal to 180°, less than or equal to 120°, less than or equal to 90°, less than or equal to 45°, or less than or equal to 15°. The integrated device dies 22, 26, 34, 36 can comprise any suitable type of device die, such as a processor die, a sensor die, a microelectromechanical systems (MEMS) die, a memory die, etc. The integrated device dies 22, 26, 34, 36 can be electrically connected to the package substrate 20 in any suitable manner. For example, the dies 22, 26, 34, 36 can electrically connect to the package substrate 20 by way of a flip-chip connection or a wire bond connection. In the illustrated embodiments, the dies 22, 26, 34, 36 can be flip-chip mounted to the substrate 20 by way of an intervening adhesive, such as solder, a conductive epoxy, non-conductive paste, anisotropic conductive film, etc. Similar mounting techniques can be employed to mount the dies 22, 26, 34, 36 with contacts on their bottom sides connected, for example, to through silicon vias (TSVs).

Referring again to FIG. 1, in certain treatment procedures, the catheter assembly 10, with the integrated device package 3 disposed therein, may be inserted into a vessel of the patient (e.g., inserted into the femoral artery) and guided through the vasculature to the target location 16 (e.g., the heart or other location in the body). To reach the target location 16, the catheter assembly 10 may traverse numerous turns and forks, and may generally bend at multiple locations and at multiple angles in multiple orientations during the procedure. It can be challenging to incorporate integrated device dies in such a catheter assembly 10 since the relative stiffness of the dies may reduce the flexibility of the catheter assembly 10.

Referring again to FIGS. 2 and 3, beneficially, therefore, the bendable segment 30 disposed between the first and second segments 24, 28 can enable the package 2 to bend in a piecewise fashion as the catheter assembly 10 traverses the anatomy. For example, the first and second segments 24, 28 may be relatively stiff, but may also be sufficiently small so as to traverse the bends and turns of the vasculature or other body lumen. For example, in various embodiments, the first and second segments 24, 28 (which may be defined by the length of the integrated device dies 22, 26) may have lengths along the longitudinal axis L in a range of 1 mm to 8 mm, in a range of 1 mm to 5 mm, in a range of 2 mm to 5 mm, etc. During use, the integrated device dies 22, 26, 34, 36 and first and second segments 24, 28 may bend relative to one another about one or more axes so as to position the dies 22, 34 at multiple orientations and angles relative to the dies 26, 36. In various embodiments, for example, the bendable segment 30 may bend and/or twist about an axis T transverse to the longitudinal axis L so as to angle the dies 22, 34 relative to the dies 26, 36 about the transverse axis T. In various embodiments, the bendable segment 30 may bend and/or twist about the longitudinal axis L so as to angle the dies 22, 34 relative to the dies 26, 36 about the longitudinal axis L. Although the segment 24 of FIG. 3 is illustrated as being bent downwardly in FIG. 3, the segment 24 may also bend upwardly about the transverse axis T, and/or may twist about the longitudinal axis L.

As shown in FIGS. 2 and 3, the integrated device package 3 may also include a flap 32 opposite the bendable segment 30 to provide more volume for electronics 62 while maintaining flexibility of the catheter assembly 10. These electronics 62 may comprise passive components, such as resistors, capacitors, inductors, and/or may comprise integrated device dies. Advantageously, the electronics 62 can be mounted to the flap 32 and disposed between the flap 32 and the bendable segment 30, which may be spaced from and generally parallel to the bendable segment 30. In some embodiments, the electronics 62 may not be mounted to the bendable segment 30, e.g., the electronics 62 may be permitted to move relative to the bendable segment 30. During insertion of the catheter assembly 10 into the patient, the bendable segment 30 can bend about any direction without interference from the electronics 62, since the electronics 62 may not be mechanically attached to the bendable segment 30; the electronics 62 may be mechanically attached to the flap 32. In FIG. 2, the flap 32 is bent about the longitudinal axis so as to position the flap 32 opposite from (e.g., generally parallel to) the bendable segment 30. The flap 32 can have any suitable length in the longitudinal axis L so long as the flap 32 does not interfere with other components of the package 3. For example, in some embodiments, the flap 32 can have lengths along the longitudinal axis L in a range of 0.5 mm to 10 mm, in a range of 0.5 mm to 5 mm, in a range of 2 mm to 5 mm, etc. In some embodiments, the flap 32 can include flexible segments between the electronics 62.

Figure 4:
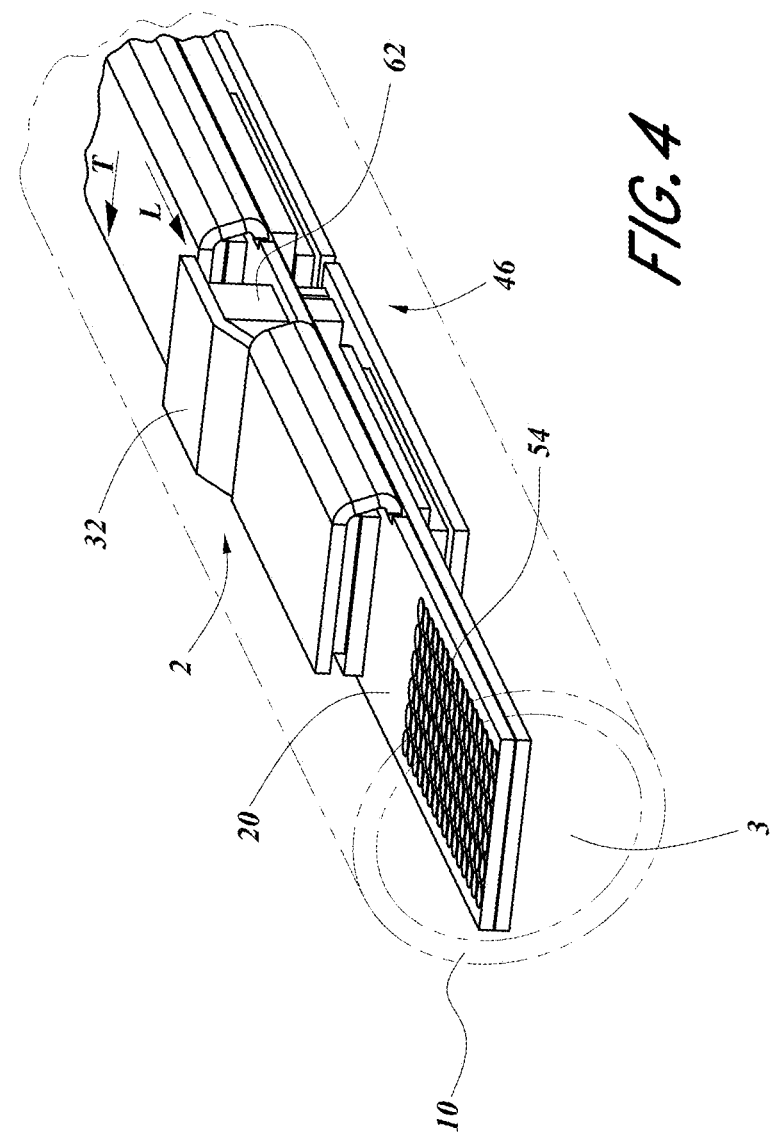
FIG. 4 is a perspective view of an integrated device package with two package modules disposed in a catheter assembly seen from a distal portion.

FIG. 4 shows another perspective view of the integrated device package 3 having two package modules 2, 46 (see also FIG. 5) as seen from a distal portion 4, including the flap 32 and electronics 62. In FIG. 3, for example, the flap 32 may extend outwardly from the bendable segment 30 and can bend about the axis T transverse to the longitudinal axis L. The electronics 62 can be mounted to the flap 32, such that the bendable segment 30 can bend without interference from the electronics 62.

Figure 5:
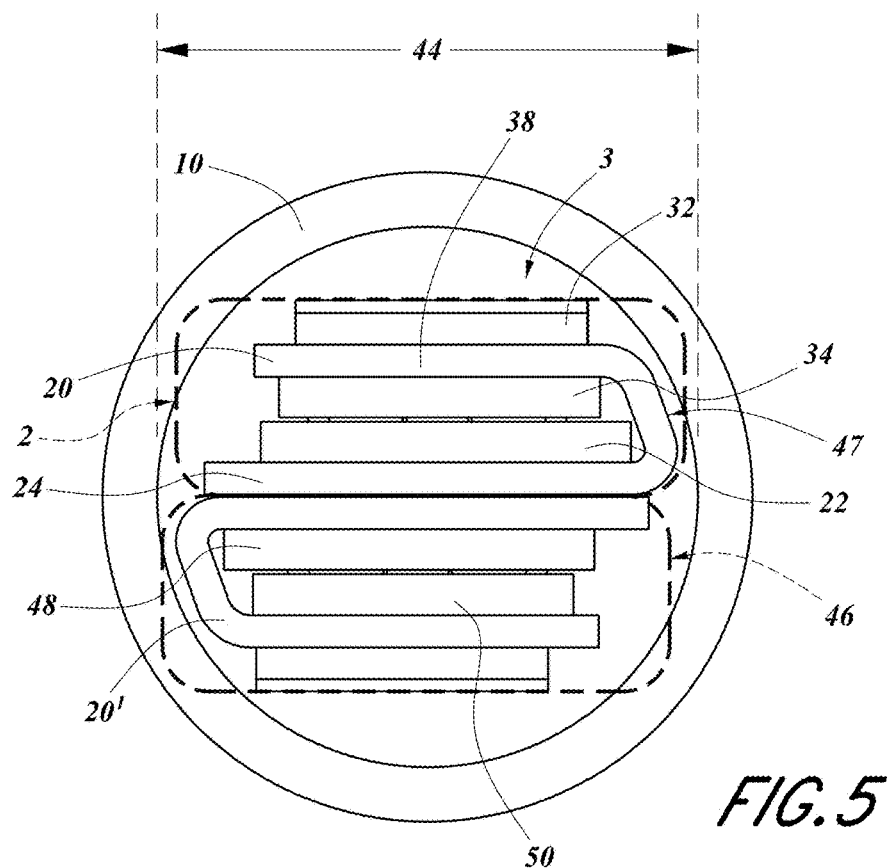
FIG. 5 is a schematic cross-section view of the integrated device package with two package modules of FIGS. 3-4, with the cross-section taken transverse to a longitudinal axis, according to an embodiment.

FIG. 5 is a schematic cross-section view of the integrated device package 3 disposed in a catheter assembly 10, with the cross-section taken transverse to the longitudinal axis L, according to another embodiment. The integrated device package 3 can comprise the package module 2 illustrated in FIGS. 1-4 mounted to a second package module 46. In FIG. 5, the respective package modules 2, 46 are delimited by a dashed line for ease of reference. The second package module 46 may be substantially similar to or the same in configuration as the package module 2, but may have different devices therein. As shown in FIG. 5, the third integrated device die 34 can be mounted and electrically connected to the third segment 38 of the package substrate 20, and the first integrated device die 22 can be mounted and electrically connected to the first segment 24 of the package substrate 20. The integrated device dies of the second module 46 may likewise be mounted to corresponding segments of a second package substrate 20'. As shown in FIG. 5, the package substrates 20, 20' can be mounted back to back within the catheter assembly 10. In some embodiments, the substrates 20, 20' can be adhered to one another. In some embodiments, the substrates 20, 20' can electrically connect to one another, e.g., by way of conductive adhesive. In some embodiments, the modules 2, 46 may share the bendable segment 30 (see FIG. 2) to connect the modules 2, 46 to other modules along the longitudinal axis L (into and out of the page in the view of FIG. 5). Thus, both modules 2, 46 can bend at generally the same locations, e.g., at corresponding bendable segments 30 of each module 2, 46. As shown in FIG. 5, the package substrates 20, 20' can be bent about a direction parallel to the longitudinal axis L such that the third and first integrated device dies 34, 22 are disposed between the third and first segments 38, 24. A transverse dimension of the integrated device package 3 on the transverse axis T, transverse to the longitudinal axis L, can be in a range of 0.5 mm to 6 mm, in a range of 0.5 mm to 5 mm, in a range of 0.5 mm to 3 mm, in a range of 0.5 mm to 2.5 mm, in a range of 1 mm to 3 mm, in a range of 1 mm to 2.5 mm, or in a range of 1.5 mm to 3 mm, e.g., about 2 mm in some embodiments. In some embodiments, the transverse dimension of the integrated device package 3 at the bendable segment 30 can be smaller than the transverse dimension at or near the first and/or second segment 24, 28. In some embodiments, the transverse dimensions of the first segment 24 and the third segment 38 can be different to be shaped to fit in the catheter assembly 10 with less wasted space in the catheter assembly 10 than there would be if the transverse dimensions of the first and third segments 24, 38 were the same. That is, as shown in FIG. 5, the segment 38 can be narrower than the segment 24 such that the segment 38 can better conform to the rounded boundary of the catheter assembly 10. Similarly, the transverse dimensions of the flap 32 can be different from the first segment 24 and/or the third segment 38.

The package substrate 20 may be bent about a direction parallel to the longitudinal axis L at an angle of 170° to 190°. For example, a folded region 47 can position the segments 38, 24 at an angle about the longitudinal axis L. Unlike the bendable segment 30, in various embodiments, the folded region 47 can be fixed relative to the longitudinal axis L. For example, the integrated device package 3 may further include a molding compound between at least portions of the third and first integrated device dies 34, 22 to mechanically couple them and to maintain their positions relative to one another during the treatment procedure. In some embodiments, the molding compound can act as a cushion or stress buffer, may seal against contamination or moisture, and/or may protect the dies 34, 22 from mechanical damage. The package module 2 may be coupled with the second package module 46, such that the bottom segment of the top module 2 and the top segment of the lower module 46 are adjacent to each other, as shown in FIG. 5. Similar to the module 2, the second module 46 may comprise a fifth integrated device die 48 and a sixth integrated device die 50, shown in FIG. 5, mounted and electrically connected to corresponding segments of the second package substrate 20'.

Figure 6:
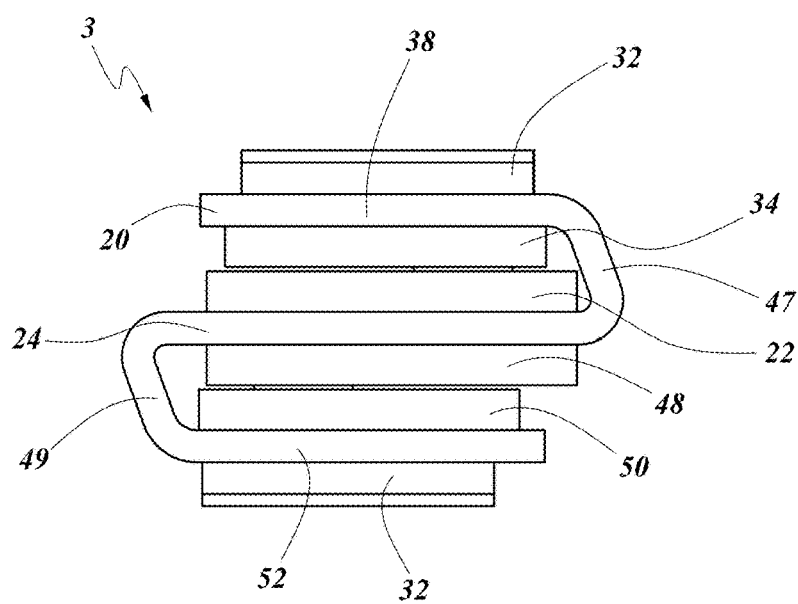
FIG. 6 is a schematic end view of a package with a package module having two folded regions according to an embodiment.

FIG. 6 is a schematic end view of a package 3 according to another embodiment. Unlike in FIG. 5, which illustrates two substrates 20, 20' positioned within the catheter assembly 10, in FIG. 6, only a single substrate 20 may be used with multiple bends at two folded regions 47, 49 about the longitudinal axis L (into and out of the page in the view of FIG. 6). In FIG. 6, the third integrated device die 34 is mounted to the third segment 38, the fifth integrated device die 48 is mounted to the first segment 24 such that the first and fifth integrated device dies 22, 48 are on opposite sides of the first segment 24, and the sixth integrated device die 50 is mounted and electrically connected to a fifth segment 52 of the package substrate 20. In such an embodiment, the package substrate 20 can be bent at a second folded region 49 such that the fifth and sixth integrated device dies 48 and 50 are disposed between the first and fifth segments 24 and 52.

Beneficially, the transverse dimension (the smallest outside dimension of the packages 3, parallel to transverse axis T) shown in FIGS. 5 and 6 can have a maximum dimension that is sized and shaped to fit within a catheter assembly 10 or width 44, as explained above. As shown in FIG. 6, the outermost segments of the package substrate 20, such as the segments 38 and 52, can have lateral dimensions along the transverse axis T that are less than corresponding lateral dimensions of the interior segments, such as segment 24. Dimensioning the segments 38, 52 to be narrower than the segment 24 can enable the package 3 to fit within a rounded structure, such as a catheter assembly 10, while maximizing the number of devices that can be mounted. Moreover, the folded regions 47, 49 can be shaped so as to fit within the rounded structure. As shown in FIG. 5, the folded region 47, 49 can be folded so as to generally conform to the curvature of the catheter assembly 10.

Figure 7:
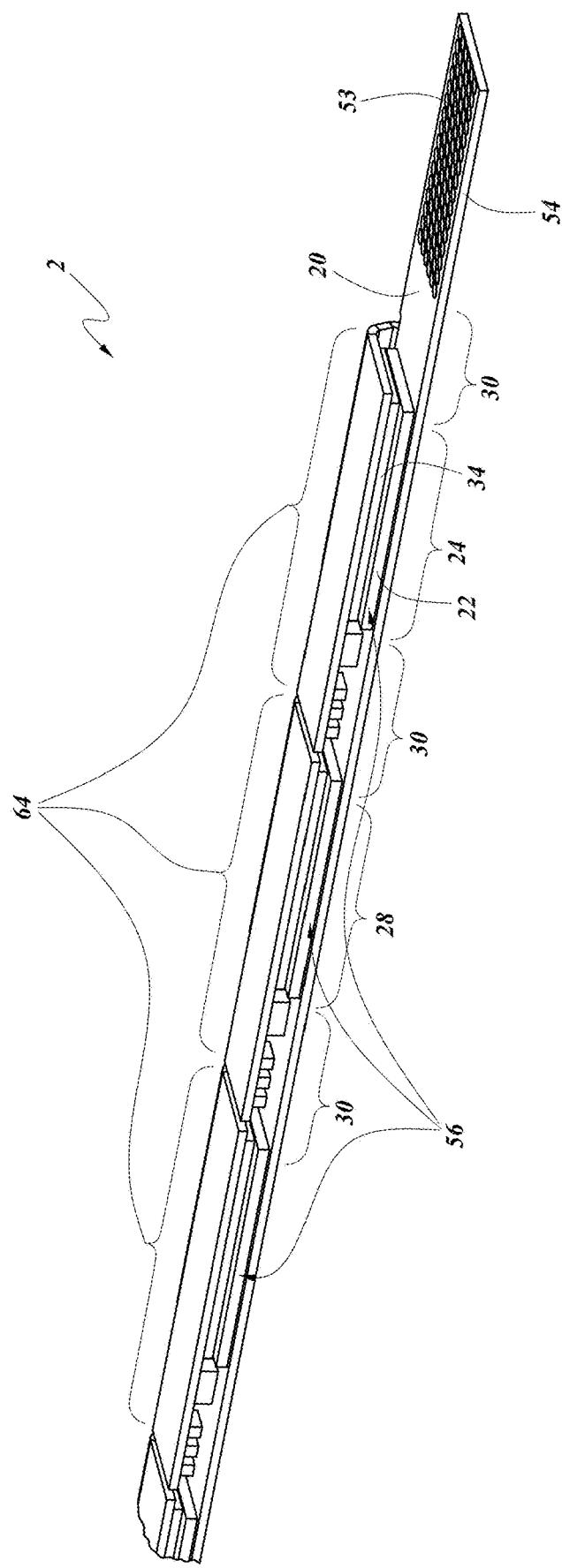
FIG. 7 is a top perspective view of a distal portion of a package module for a catheter assembly.

FIGS. 7 and 8 are top perspective views of a package module 2 for a catheter assembly 10. In particular, FIG. 7 illustrates a distal portion of the package module 2, and FIG. 8 illustrates a proximal portion of the package module 2. The package module 2 shown in FIGS. 7 and 8 can be the same as or generally similar to the modules 2, 46 described above. As shown in FIG. 7, at the distal portion, the package module 2 can include a first plurality of electrodes 53 at a distal segment 54 of the elongated package substrate 20. The electrodes 53 can be configured for use in any suitable treatment procedure. For example, in some embodiments, the electrodes 53 can be configured for mounting and electrically connecting a device for use in ECG procedures to measure the electrical output of the patient's heart. In some embodiments, the electrodes 53 can be configured for mounting and electrically connecting a device for use in cardiac ablation procedures. Still other uses for the electrodes 53 may be suitable. Although electrodes 53 are illustrated in FIG. 7, it should be appreciated that any suitable type of interactive device 13 (FIG. 1) can be provided at the distal portion of the package module 2. For example, as explained above, the interactive device can comprise any suitable type of sensor or actuation mechanism used to treat the patient. In some embodiments, there can be a bendable segment 30 between the first segment 24 and the distal segment 54. The bendable segment 30 between the first segment 24 and the distal segment 54 can be the same or generally similar to the bendable segment 30 disposed between the first and second segments 24, 28. The bendable segment 30 between the first segment 24 and the distal segment 54 can bend so as to angle the first device unit relative to the plurality of electrodes at a plurality of orientations. Similarly, as shown in FIG. 8, in some embodiments, there can be another bendable segment 30 between the proximal segment and a last segment 68 that holds one of the device dies 56.

The electrodes 53 shown in the module 2 of FIG. 7 provide N channels to be processed by the device 1. In the illustrated embodiment, the distal segment 54 of the package module 2 comprises 96 channels. When two modules 2, 46 are provided in the catheter assembly 10, therefore, the total number of channels can be 192. It should be appreciated, however, that any suitable number of channels may be provided by each module 2, 46. For example, each module 2, 46 can comprise electrodes 53 that provide between 32 and 768 channels for the device 1. With high channel counts, it can be challenging to route the signals to and/or from the console 11 outside the patient. As explained above, if wires are used to route each channel outside the patient, then the resulting wire bundle may be stiff and difficult to insert into the anatomy. Moreover, routing analog signals along the length of the catheter assembly 10 may result in signal losses or otherwise may degrade the signal integrity. In some embodiments, the electrodes 53 can be provided in a form of a port or a connector for easily attaching/detaching any suitable type of interactive device 13 (FIG. 1).

Beneficially, the embodiments disclosed herein position the device dies 56 (which may be the same as or similar to the dies described above) near the distal portion of the catheter assembly 10 so as to process the signals transferred to and/or from the electrodes 53 and the interactive device 13 (FIG. 1). Such pre-processing capabilities within the catheter assembly 10 can improve signal integrity and can reduce the number of signals being output to the console 11. Indeed, as shown in FIG. 8, the proximal portion of the package module 2 can comprise a proximal segment 60 that includes a second plurality of contact pads 58. Each pair of opposing device dies (such as die pairs 22, 34 and die pairs 26, 36) can define a device unit 64 (FIG. 7) at a particular location along the longitudinal axis L. A plurality of device units 64 can be spaced apart along the longitudinal axis L, and, as explained above, can be separated by respective bendable segments 30. Each device unit 64 can be configured to process one or a plurality of channels corresponding to one or a plurality of the electrodes 53 at the distal portion of the module 2. For example, in some embodiments, one die (such as the die 22) can comprise a high voltage chip, and the other die (such as die 34) can comprise a low voltage chip. The device unit 64 defined by the die pair (such as the die pair 22, 34) can process one or more channels, e.g., can perform one or more of analog-to-digital conversion, muxing, and amplification to each channel. In some embodiments, each device unit 64 can process 3 channels, for example. As explained above, if the illustrated module 2 is associated with 96 channels, and if each device unit 64 can process three channels, then the illustrated module 2 can comprise 32 device units 64 spaced apart along the longitudinal axis L in order to process the 96 channels. The other module 46 can be similarly arranged to process the other 96 channels. It should be appreciated that each module and/or device unit 64 can process any suitable number of channels, and that the numbers used herein are examples.

For example, FIG. 9 illustrates 32 device units 64 of each of the modules 2, 46 spaced along the longitudinal axis L within the catheter assembly 10. The package 3 shown in FIG. 9 can have a length l along the longitudinal axis L in a range of 5 mm to 500 mm, in a range of 5 mm to 300 mm, in a range of 5 mm to 250 mm, in a range of 50 mm to 300 mm, in a range of 50 mm to 250 mm, in a range of 100 mm to 300 mm, in a range of 100 to 250 mm, e.g., about 225 mm in some embodiments. The package 3 can therefore be relatively long so as to accommodate numerous integrated device dies, which can beneficially increase the processing capabilities within the catheter assembly 10, while also maintaining sufficient flexibility for use within the anatomy. Though the package 3 may have the same number of device units 64 for the modules 2, 46, in some embodiments, the modules 2, 46 may have different number of device units 64. In such embodiments, one of the modules 2, 46 (e.g., the module with the larger number of device units 64) may define the length l of the package.

As shown in FIG. 8, because the device dies 56 can be used to process signals associated with the N channels, the second plurality of contact pads 58 can be fewer than the first plurality of electrodes 53 (FIG. 7). In various embodiments, a ratio of the first plurality of electrodes and the second plurality of contact pads can be in a range of 4 to 256, in a range of 4 to 128, in a range of 4 to 64, in a range of 4 to 32, or in a range of 4 to 16. In some embodiments, for example, the ratio of the first plurality of electrodes to the second plurality of contact pads can be 8. As an example, in the embodiment shown in FIG. 8, each device module (such as device module 2) can have 12 contact pads 58 and 96 electrodes 53, for a ratio of 96:12, or 8. As explained herein, the plurality of integrated device dies 56 can be configured to process signals transduced by the first plurality of electrodes 53 and to transmit the processed signals to the second plurality of contact pads 58. The processed signals can in turn be transferred to the console 11 in any suitable manner. In some embodiments, wires can be connected to the contact pads 58 and can extend proximally through the catheter assembly 10 to the console 11. Advantageously, the reduced output provided by the processing capabilities of the device dies 56 can reduce the number of wires used to route the processed signals to the console 11, and can accordingly improve the flexibility of the device. In some systems, the improved flexibility may be beneficial because it can improve the maneuverability of the device 1 within the patient's body during operation and/or use of the device 1.

Although disclosed in the context of certain embodiments and examples, it will be understood by those skilled in the art that the present invention extends beyond the specifically disclosed embodiments to other alternative embodiments and/or uses and obvious modifications and equivalents thereof. In addition, while several variations have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the present disclosure. It should be understood that various features and aspects of the disclosed embodiments can be combined with, or substituted for, one another in order to form varying modes of the disclosed invention. Thus, it is intended that the scope of the present invention herein disclosed should not be limited by the particular disclosed embodiments described above, but should be determined only by a fair reading of the aspects that follow.

What is claimed is:

1. An integrated device package sized and shaped to be disposed in a catheter assembly, the integrated device package comprising:
a package substrate;
a first integrated device die mounted and electrically connected to a first segment of the package substrate, the first integrated device die having a first side facing the first segment of the package substrate and a second side opposite the first side;
a second integrated device die mounted and electrically connected to a second segment of the package substrate, the second integrated device die spaced from the first integrated device die along a longitudinal axis of the package substrate; and
a third integrated device die disposed over the second side of the first integrated device die, wherein the first integrated device die and the third integrated device die at least partially overlap along the longitudinal axis, wherein the package substrate comprises a bendable segment positioned between the first segment and the second segment, the integrated device package being configured such that, during use of the integrated device package in the catheter assembly, the bendable segment bends so as to angle the first integrated device die relative to the second integrated device die at a plurality of orientations.

2. The integrated device package of claim 1, further comprising a flap and one or more electronic components mounted to the flap, the flap being disposed between the first and second segment in the longitudinal axis and spaced from the bendable segment in a transverse axis transverse to the longitudinal axis.

3. The integrated device package of claim 1, further comprising a third segment of the package substrate and the third integrated device die is mounted on the third segment, the third segment bent relative to the first segment along an axis parallel to the longitudinal axis so as to position the third integrated device die at an angle relative to the first integrated device die.

4. The integrated device package of claim 3, wherein the third segment is bent so as to position the third integrated device die at an angle of 170° to 190° relative to the first integrated device die and the first and third integrated device dies are disposed between the first and third segments.

5. The integrated device package of claim 3, wherein the first integrated device die and the third integrated device die define a first device unit.

6. The integrated device package of claim 5, wherein the package substrate, the first device unit and a second device unit comprising the second integrated device die define a first package module, the integrated device package further comprising a second package module including a third device unit comprising fourth and fifth integrated device dies mounted on respective fourth and fifth segments of a second package substrate.

7. The integrated device package of claim 6, wherein the first and second package modules further comprising a plurality of device units.

8. The integrated device package of claim 6, wherein the package module and the second package module are disposed adjacent one another along an axis transverse to the longitudinal axis.

9. The integrated device package of claim 1, wherein a lateral dimension of the integrated device package is less than 6 mm, the lateral dimension being a dimension transverse to the longitudinal axis.

10. The integrated device package of claim 1, wherein the package substrate comprises a flexible insulating sheet with embedded conductors.

11. The integrated device package of claim 1, wherein at least one of the first and second dies performs an analog-to-digital conversion (ADC).

12. An integrated device package sized and shaped to be disposed in a catheter assembly having a longitudinal axis and a transverse axis transverse to the longitudinal axis, the integrated device package comprising:
a package substrate comprising a first segment, a second segment, a third segment and a bendable segment;
a first integrated device die mounted and electrically connected to the first segment of the package substrate; and
a second integrated device die mounted and electrically connected to the second segment of the package substrate, wherein the package substrate is bent about the longitudinal axis such that the first and second integrated device dies are disposed between the first and second segments,
wherein the bendable segment is disposed along the longitudinal axis of the catheter assembly between the first segment and the third segment, such that, during use of the integrated device package in the catheter assembly, the bendable segment bends so as to angle the first integrated device die relative to the third segment at a plurality of orientations about the transverse axis.

13. The integrated device package of claim 12, wherein the first and second integrated device dies define a first device unit.

14. The integrated device package of claim 13, wherein the package substrate and the first device unit define a first package module, the integrated device package further comprising a second package module including a second device unit comprising third and fourth integrated device dies disposed between respective fourth and fifth segments of a second package substrate.

15. The integrated device package of claim 14, wherein the first package module and the second package module are disposed adjacent one another along a second transverse axis transverse to the longitudinal axis and perpendicular to the transverse axis.

16. The integrated device package of claim 14, wherein the first package module further comprising a third device unit and a second bendable segment positioned between the first and third device units.

17. A package for a catheter assembly comprising:
an elongate package substrate having a major longitudinal dimension;
an interactive device comprising a first plurality of electrodes at a distal portion of the elongate package substrate, the interactive device configured to interact with a target location of a human patient;
a second plurality of contact pads at a proximal portion of the elongate package substrate, the second plurality being fewer than the first plurality; and
a plurality of integrated device dies mounted to the package substrate between the distal and proximate portions of the elongate package substrate, the plurality of integrated device dies configured to process signals transduced by the first plurality of electrodes and to transmit the processed signals to the second plurality of contact pads, or to process signals received from the second plurality of contact pads and to transmit the processed signals to the first plurality of electrodes,
wherein a first integrated device die of the plurality of integrated device dies is mounted to a first segment of the elongate package substrate and a second integrated device die of the plurality of integrated device dies is mounted to a second segment of the elongate package substrate, the first segment and the second segment being longitudinally spaced by a bendable segment so as to angle the first integrated device die relative to the second integrated device die at a plurality of orientations about a transverse dimension that is transverse to the major longitudinal dimension, and
wherein the plurality of integrated device dies further comprises a third integrated device die mounted on a third segment of the elongate package substrate, wherein the package substrate is bent about the longitudinal axis such that the first die and the third die are disposed between the first segment and the third segment.

18. The package of claim 17, wherein at least one of the plurality of integrated device dies is configured to perform an analog-to-digital conversion (ADC).

19. The package of claim 17, wherein the first and third integrated device dies define a first device unit, the package substrate and the first device unit define a first package module, the integrated device package further comprising a second package module including a second device unit comprising fourth and fifth integrated device dies disposed between respective fourth and fifth segment of a second package substrate.

20. The package of claim 17, wherein the first plurality of contact pads are connected to a sensor or an actuator.

21. The package of claim 17, wherein the package is configured such that, during use of the package in the catheter assembly, the bendable segment bends so as to angle the first integrated device die relative to the second integrated device die at a plurality of orientations.

22. The package of claim 17, further comprising a flap and one or more electronic components mounted to the flap, the flap being disposed between the first and second segments and spaced from the bendable segment in a transverse axis transverse to the major longitudinal direction.

23. The package of claim 19, wherein the first package module and the second package module are disposed adjacent one another along a second transverse dimension transverse to the longitudinal dimension and perpendicular to the transverse dimension.

* * * * *